United States Patent [19]

Carville

[11] Patent Number: 4,460,703

[45] Date of Patent: Jul. 17, 1984

[54] CATALYST FOR EPOXIDE POLYMERIZATION

[75] Inventor: Donna B. Carville, Plaquemine, La.

[73] Assignee: The Dow Chemical Company, Midland, Mich.

[21] Appl. No.: 485,989

[22] Filed: Apr. 18, 1983

[51] Int. Cl.³ .............................................. B01J 31/14
[52] U.S. Cl. ..................................... 502/155; 528/416
[58] Field of Search ......................................... 502/155

[56] References Cited

U.S. PATENT DOCUMENTS

| | | | |
|---|---|---|---|
| 3,065,188 | 11/1962 | Vandenberg | 528/416 X |
| 3,135,705 | 6/1964 | Vandenberg | 502/152 X |
| 3,135,706 | 6/1964 | Vandenberg | 502/155 X |
| 3,186,958 | 6/1965 | Kutner et al. | 528/393 X |
| 3,219,591 | 11/1965 | Vandenberg | 502/152 |
| 3,396,125 | 8/1968 | Wolford | 528/393 |
| 3,457,197 | 7/1969 | Hsieh | 502/153 X |
| 3,484,388 | 12/1969 | Wolford | 502/154 X |
| 3,499,847 | 3/1970 | Mange | 528/393 |
| 3,506,597 | 4/1970 | Asai | 528/393 X |
| 3,642,667 | 2/1972 | Steller | 502/156 X |
| 3,712,870 | 1/1973 | Guillot | 502/155 X |

*Primary Examiner*—Patrick Garvin
*Attorney, Agent, or Firm*—Douglas N. Deline

[57] ABSTRACT

A novel composition of matter for catalyzing the polymerization of vicinal epoxides is formed by the reaction of a trialkylaluminum compound, phenothiazine, water, acetylacetone and a Lewis base selected from tetrahydrofuran and 1,4-dioxane.

2 Claims, No Drawings

CATALYST FOR EPOXIDE POLYMERIZATION

BACKGROUND OF THE INVENTION

The present invention relates to a novel catalyst composition useful to the polymerization of epoxides. More particularly, the present invention is an aluminum-based coordination catalyst having improved catalytic activity for the preparation of homopolymers and copolymers of epoxides. The improved catalysts demonstrate improved rates of polymerization compared to previously known catalysts. The catalysts suitably may be employed to produce polymerized vicinal epoxides of extremely high molecular weights.

SUMMARY OF THE INVENTION

According to the present invention, there is provided an improved aluminum-based coordination catalyst for the polymerization of vicinal alkylene oxides comprising the reaction product of:
(1) a trialkylaluminum compound corresponding to the formula $Al(R)_3$ wherein R is independently each occurrence a lower alkyl radical;
(2) phenothiazine;
(3) a Lewis base selected from the group consisting of 1,4-dioxane and tetrahydrofuran;
(4) water; and
(5) acetylacetone,
wherein the ratio in moles of trialkylaluminum compound/phenothiazine/Lewis base/water/acetylacetone are from about 1.0/0.1/1.0/0.2/0.2 to about 1.0/1.0/6.0/1.0/1.0.

DETAILED DESCRIPTION OF THE INVENTION

The catalyst of the instant invention is more particularly described as follows. The trialkylaluminum compound is suitably trimethylaluminum, triethylaluminum, triisopropylaluminum, etc. The trialkylaluminum compound is generally reacted with a solution of at least one or more of phenothiazine, the Lewis base or acetylacetone in an inert solvent. Suitable inert solvents include aromatic liquids, especially toluene, or more preferably saturated hydrocarbons, especially hexane.

The remaining components are then added in any order desired. All additions are preferably accomplished with vigorous stirring over a sufficiently long period of time to prevent localized overheating of the reaction mixture and at a suitable reduced temperature. Satisfactory temperatures for the addition are from about $-10°$ C. to about $30°$ C.

While the components may be combined in any sequence, it is preferred in order to provide the most effective catalyst, to first combine the trialkylaluminum compound with phenothiazine, then add the Lewis base followed by water and finally acetylacetone.

It should be remembered in adding water that small quantities of water may be present in the solvents and other reactants employed. Accordingly, analysis of the reaction mixture for water content prior to addition of water will aid in adding only the exact amount of water required.

Preferably the components are added such that, except for the Lewis base, no excess of coordinating compounds, e.g., phenothiazine, water and acetylacetone, occurs, based on the number of equivalents of trialkylaluminum present. It is believed without wishing to be bound by such belief that all three alkyl moieties of the aluminum alkyl are replaced during formation of the aluminum-based coordination catalyst of the invention. The Lewis base may be present in an excess of up to about 8 moles for each mole of trialkylaluminum originally present. However, large excesses of Lewis base compound are considered to be detrimental (possibly due to the presence of reactive hydrogen-containing compounds like water or alcohol) and should be avoided.

An additional component such as an ether alcohol may be added to the reaction mixture in small quantities, particularly in partial replacement for small amounts of phenothiazine or water component. However, generally no benefit is believed to arise from such substitution. Suitable ether alcohols include ethoxyethanol, methoxyethanol, butoxyethanol, diethylene glycol methyl ether, etc.

After addition of all catalyst components is complete, it may be desirable to allow all components to reach an equilibrium state. This may be accomplished by allowing the catalyst composition to age, optionally at elevated temperatures of up to about $100°$ C. Generally, maintaining the reaction mixture at such an elevated temperature for a period of about one hour is sufficient to provide uniformly active catalysts.

The polymerization process for vicinal epoxides is essentially the same as is already known in the art. Generally, the catalyst and vicinal epoxide are contacted, optionally at slightly elevated temperatures, in the presence of an inert diluent such as a hydrocarbon diluent. The epoxide may be purified prior to polymerization by any suitable means such as the technique disclosed in U.S. Pat. No. 3,987,065, which teaching is incorporated herein by reference. Further detailed description of the polymerization process may be found by reference to U.S. Pat. Nos. 3,219,591; 3,642,667; 3,580,938 or 3,186,958, the teachings of which are incorporated herein by reference.

Epoxides that may be polymerized according to the instant invention are vicinal epoxides of up to about 10 carbons selected from the group consisting of vicinal alkylene oxides, substituted alkylene oxides and glycidyl ethers. Exemplary are ethylene oxide, propylene oxide, 1,2-butylene oxide, isobutylene epoxide, epichlorohydrin, epibromohydrin, vinylchloride epoxide, tertiary butyl glycidyl ether, methyl glycidyl ether, n-octyl glycidyl ether, phenyl glycidyl ether, alkylphenyl glycidyl ether, etc.

The polymerized epoxides formed employing the present catalysts are highly useful as additives to provide impact resistant properties to polymers such as polystyrene or polyvinylchloride and as an additive to hydrocarbon liquids such as jet fuels to prevent atomization or mist formation upon application of shearing forces.

SPECIFIC EMBODIMENTS

Having described the invention, the following examples are provided as further illustrative and are not to be construed as limiting.

EXAMPLE 1

In a dry glass reaction flask with a nitrogen purge, triisobutyl aluminum (0.015 mole) is added with stirring to a solution of phenothiazine (0.004 mole) in hexane (33 g) at ambient temperature. Tetrahydrofuran (0.090 mole) is added dropwise with stirring over a period of about 10 minutes at a reduced temperature of about 0° C.–10° C. Next, a mixture of water (enough to provide about 0.006 mole total water), acetylacetone (0.006 mole) and hexane (5 ml) is added. The reaction mixture is stirred for about an additional hour at ambient temperature then transferred to a Paar bomb and diluted with hexane (100 ml). After aging by heating and stirring under nitrogen atmosphere an additional hour, the catalyst preparation is complete.

The catalyst is employed to polymerize 1,2-epoxybutane. Accordingly, one mole of 1,2-butylene oxide is added to the catalyst solution at 75° C. in increments over a one-hour period. The reaction mixture is stirred for an additional 5 hours at 75° C. and then cooled. The catalyst is neutralized by the addition of about 2 ml of methanol. Evaporation of the solvent leaves the desired polymer, a light amber colored rubbery solid.

What is claimed is:

1. A composition of matter consisting essentially of the reaction product of:
   (1) a trialkylaluminum compound corresponding to the formula $Al(R)_3$ wherein R is independently each occurrence a lower alkyl radical;
   (2) phenothiazine;
   (3) a Lewis base selected from the group consisting of 1,4-dioxane and tetrahydrofuran;
   (4) water; and
   (5) acetylacetone,
wherein the ratio in moles of trialkylaluminum compound/phenothiazine/Lewis base/water/acetylacetone is from about 1.0/0.1/1.0/0.2/0.2 to about 1.0/1.0/6.0/1.0/1.0.

2. A composition of matter according to claim 1 wherein the trialkylaluminum compound is triisobutylaluminum.

* * * * *